US009604211B2

(12) United States Patent
Seo et al.

(10) Patent No.: US 9,604,211 B2
(45) Date of Patent: Mar. 28, 2017

(54) MICRO-CHIP FOR DIAGNOSIS AND INTEGRATED ROTARY DIAGNOSIS METHOD USING THE SAME

(71) Applicant: KOREA ADVANCED INSTITUTE OF SCIENCE AND TECHNOLOGY, Daejeon (KR)

(72) Inventors: Tae Seok Seo, Daejeon (KR); Jae Hwan Jung, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 128 days.

(21) Appl. No.: 14/557,890

(22) Filed: Dec. 2, 2014

(65) Prior Publication Data

US 2015/0292038 A1 Oct. 15, 2015

(30) Foreign Application Priority Data

Apr. 11, 2014 (KR) ........................ 10-2014-0043664

(51) Int. Cl.
*C12Q 1/68* (2006.01)
*C12P 19/34* (2006.01)
(Continued)

(52) U.S. Cl.
CPC ......... *B01L 3/50273* (2013.01); *B01L 7/5255* (2013.01); *B01L 2200/10* (2013.01); *B01L 2300/0803* (2013.01); *B01L 2300/0867* (2013.01); *B01L 2300/0883* (2013.01); *B01L 2300/1827* (2013.01); *B01L 2400/0409* (2013.01); *B01L 2400/0688* (2013.01)

(58) Field of Classification Search
None
See application file for complete search history.

(56) References Cited

U.S. PATENT DOCUMENTS 7,384,602 B2 * 6/2008 Nagaoka ........... B01L 3/502738 422/50

OTHER PUBLICATIONS

Jae Hwan Jung et al., "Integrated centrifugal reverse transcriptase loop-mediated isothermal amplification microdevice for influenza A virus detection", Biosensors and Bioelectronics, 2015, pp. 218-224, vol. 68.

(Continued)

*Primary Examiner* — Young J Kim
(74) *Attorney, Agent, or Firm* — Rabin & Berdo, P.C.

(57) ABSTRACT

Provided is a micro-chip for diagnosis, including a unit process part located apart from a rotation center, which includes: a target substance capturing unit having a capture passage and a capturing means filling a capture passage; a sample storing unit connected to capture passage and giving an inner space in which a sample is stored; a washing buffer chamber connected to the capture passage and giving an inner space in which a washing buffer is stored; an elution buffer chamber connected to the capture passage and giving an inner space in which an elution buffer is stored; a reaction solution chamber giving a space in which a reaction solution required for a PCR process is stored; a discharge passage connected to the target substance capturing unit and the reaction solution chamber; a wasted solution chamber connected to the discharge passage; and a target substance chamber connected to the discharge passage.

7 Claims, 15 Drawing Sheets

(51) Int. Cl.
*B01L 3/00* (2006.01)
*B01L 7/00* (2006.01)

(56) References Cited

OTHER PUBLICATIONS

Maximilian Focke et al., "Microstructuring of polymer films for sensitive genotyping by real-time PCR on a centrifugal microfluidic platform", Lab Chip, 2010, pp. 2519-2526, vol. 10.
Jae Hwan Jung et al., "Ultrafast Rotary PCR system for multiple influenza viral RNA detection", Lab Chip, 2012, pp. 1598-1600, vol. 12.
Jae Hwan Jung et al., "A microbead-incorporated centrifugal sample pretreatment microdevice", Lab Chip, 2013, pp. 3383-3388, vol. 13.
Jitae Kim et al., "Passive flow switching valves on a centrifugal microfluidic platform", Sensors and Actuators B, 2008, pp. 613-621, vol. 128.

* cited by examiner

MICRO-CHIP FOR DIAGNOSIS AND INTEGRATED ROTARY DIAGNOSIS METHOD USING THE SAME

CROSS-REFERENCE TO RELATED APPLICATIONS

This application claims priority under 35 U.S.C. §119 to Korean Patent Application No. 10-2014-0043664, filed on Apr. 11, 2014, in the Korean Intellectual Property Office, the disclosure of which is incorporated herein by reference in its entirety.

TECHNICAL FIELD

The following disclosure relates to a diagnosis technique using gene analysis, and in particular, to a micro-chip for diagnosis, for detecting pathogens by means of gene analysis and an integrated rotary diagnosis method using the same.

BACKGROUND

Generally, a diagnosis method using gene analysis includes a patient sample collecting step, an RNA extracting step, a gene amplification step, an electrophoresis separation step, and a gene detecting and a distinguishing step. However, in the related art, since each step is performed by individual equipment or devices, expensive analysis devices and a large amount of samples are required. In addition, much time is consumed for analysis, the samples are highly likely to be contaminated during the analysis process, and rapid diagnosis on the spot is not available. To solve the above problems, an integrated gene analysis device using a microfluidic micro-chip has been recently developed. However, the existing integrated gene analysis has a complicated chip structure and requires metal-electrode patterning and a complicated design using a silicon/glass substrate, which results in high fabrication costs. Moreover, its operation is complex due to the need of external introduction pumps and a plurality of tube systems, the highly integrated chip driving device has low reproducibility, and the system has no automation function and also has a limit in reducing its size, which causes problems in diagnosis on the spot. Therefore, there are demanded further improvements.

SUMMARY

An embodiment of the present disclosure is directed to providing a micro-chip for diagnosis, for performing a preprocess to a sample and detecting pathogens, and an integrated rotary diagnosis method for performing gene amplification and pathogen detection.

In one general aspect, there is provided a micro-chip for diagnosis, which comprises a unit process part located apart from a rotation center, wherein the unit process part includes: a target substance capturing unit having a capture passage with an inlet and an outlet located outside of the inlet in a radial direction, and a capturing means filling the capture passage; a sample storing unit located inside of the target substance capturing unit in a radial direction, connected to the inlet of the capture passage and giving an inner space in which a sample is stored; a washing buffer chamber located inside of the target substance capturing unit in a radial direction, connected to the inlet of the capture passage and giving an inner space in which a washing buffer is stored; an elution buffer chamber located inside of the target substance capturing unit in a radial direction, connected to the inlet of the capture passage and giving an inner space in which an elution buffer is stored; a reaction solution chamber giving a space in which a reaction solution required for a polymerase chain reaction (PCR) process or an isothermal amplification process is stored; a discharge passage located outside of the target substance capturing unit and the reaction solution chamber in a radial direction, extending along a circumferential direction and connected to the target substance capturing unit and the reaction solution chamber; a wasted solution chamber located outside of the discharge passage in a radial direction and connected to the discharge passage; and a target substance chamber located outside of the discharge passage in a radial direction and connected to the discharge passage, wherein a portion of the discharge passage to which the wasted solution chamber is connected and a portion of the discharge passage to which the target substance chamber is connected are separated from each other along a circumferential direction.

A portion of the discharge passage which is connected to the capture passage may be located to face a portion of the discharge passage which is connected to the wasted solution chamber, and a portion of the discharge passage which is connected to the reaction solution chamber may be located to face a portion of the discharge passage which is connected to the target substance chamber.

A portion of the discharge passage which is connected to the capture passage and a portion of the discharge passage which is connected to the wasted solution chamber may be respectively located at both ends of the discharge passage in a circumferential direction.

The capture passage may connect the inlet and the outlet in a zigzag pattern.

The unit process part may further include a valve unit configured to surround the washing buffer chamber, the elution buffer chamber and the reaction solution chamber, and the valve unit may be a manual valve using a height difference.

The unit process part may further include an elution buffer flow control passage for introducing the elution buffer stored in the elution buffer chamber to the target substance capturing unit, and the elution buffer flow control passage may include a flow changing curved portion for changing a flow of the elution buffer from an inside to an outside in a radial direction.

The unit process part may further include a reaction solution flow control passage extending from the reaction solution chamber, and the reaction solution flow control passage may include a flow changing curved portion for changing a flow of the reaction solution discharging from the reaction solution chamber from an inside to an outside in a radial direction.

The unit process part may further include a capillary tube valve formed at a wasted solution passage which connects the discharge passage and the wasted solution chamber.

In another aspect, there is provided a diagnosis method using a micro-chip for diagnosis (hereinafter, also referred to as a 'diagnosis micro-chip'), which comprises a unit process part located apart from a rotation center including: a target substance capturing unit having a capture passage with an inlet and an outlet located outside of the inlet in a radial direction, and a capturing means filling the capture passage; a sample storing unit located inside of the target substance capturing unit in a radial direction, connected to the inlet of the capture passage and giving an inner space in which a sample is stored; a washing buffer chamber located inside of the target substance capturing unit in a radial direction, connected to the inlet of the capture passage and giving an inner space in which a washing buffer is stored; an elution buffer chamber located inside of the target substance capturing unit in a radial direction, connected to the inlet of the capture passage and giving an inner space in which an elution buffer is stored; an elution buffer flow control passage for introducing the elution buffer stored in the elution buffer chamber to the target substance capturing unit; a reaction solution chamber giving a space in which a reaction solution required for a polymerase chain reaction (PCR) process or an isothermal amplification process is stored; a reaction solution flow control passage extending from the reaction solution chamber; a discharge passage located outside of the target substance capturing unit and the reaction solution chamber in a radial direction, extending along a circumferential direction and connected to the target substance capturing unit and the reaction solution chamber; a wasted solution chamber located outside of the discharge passage in a radial direction and connected to the discharge passage; and a target substance chamber located outside of the discharge passage in a radial direction and connected to the discharge passage, wherein a portion of the discharge passage to which the wasted solution chamber is connected and a portion of the discharge passage to which the target substance chamber is connected are separated from each other along a circumferential direction, the elution buffer flow control passage includes a flow changing curved portion for changing a flow of the elution buffer from an inside to an outside in a radial direction, and the reaction solution flow control passage includes a flow changing curved portion for changing a flow of the reaction solution discharging from the reaction solution chamber from an inside to an outside in a radial direction, the method comprising: a diagnosis micro-chip preparing step for injecting a sample into the sample storing unit, injecting a washing buffer into the washing buffer chamber, injecting an elution buffer for separating a target substance from the capturing means into the elution buffer chamber, and injecting a reaction solution required for a PCR process or an isothermal amplification process into the reaction solution chamber; a preprocess step for rotating the diagnosis micro-chip to perform a preprocess to the sample and storing the target substance and the reaction solution in the target substance chamber; and an amplifying step for performing gene amplification to the target substance stored in the target substance chamber, wherein the preprocess step includes: a target substance capturing step for rotating the diagnosis micro-chip at a first rotation speed in a first rotation direction to move the wasted solution chamber toward the target substance chamber so that the sample is introduced into the target substance capturing unit; a washing buffer loading step for rotating the diagnosis micro-chip at a second rotation speed in the first rotation direction to introduce the washing buffer into the target substance capturing unit, after target substance capturing step; an elution buffer and reaction solution introducing step for reducing the rotation speed of the diagnosis micro-chip to zero (0) so that the elution buffer and the reaction solution respectively pass through the flow changing curved portion of the elution buffer flow control passage and the flow changing curved portion of the reaction solution flow control passage, after the washing buffer loading step; a reaction solution loading step for rotating the diagnosis micro-chip in a second rotation direction opposite to the first rotation direction at a third rotation speed to introduce the reaction solution into the target substance chamber, after the elution buffer and reaction solution introducing step; and an elution buffer loading step for rotating the diagnosis micro-chip at a fourth rotation speed to introduce the elution buffer into the target substance chamber, after the reaction solution loading step.

The first rotation speed may be identical to the second rotation speed.

The third rotation speed may be identical to the fourth rotation speed.

In the amplifying step, an isothermal amplification process or a PCR process may be performed.

After the amplifying step, fluorescence detection may be performed with respect to a genetic material subject to diagnosis, stored in the target substance chamber.

If the present disclosure is used, the objects of the present disclosure set forth above can be accomplished. In detail, by rotating the micro-chip for diagnosis according to the present disclosure, a preprocess and a gene amplification process are performed to a sample at a unit process part provided at the micro-chip for diagnosis, and fluorescence detection may be performed with respect to the amplified genetic material by using a gene amplification process.

DETAILED DESCRIPTION OF EMBODIMENTS

Hereinafter, exemplary embodiments will be described in detail with reference to the accompanying drawings.

Figure 1:
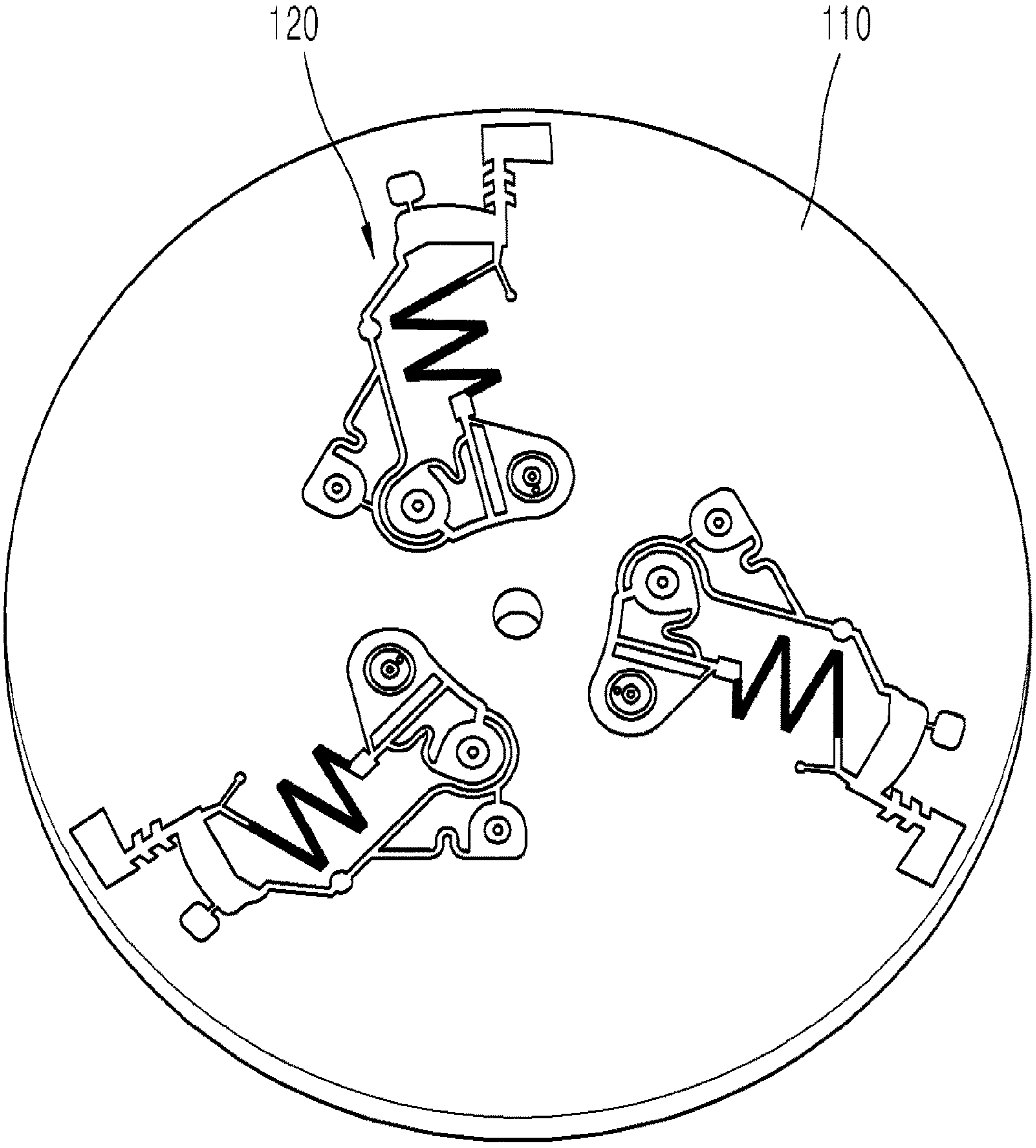
FIG. 1 is a perspective view showing a micro-chip for diagnosis according to an embodiment of the present disclosure.
Figure 2:
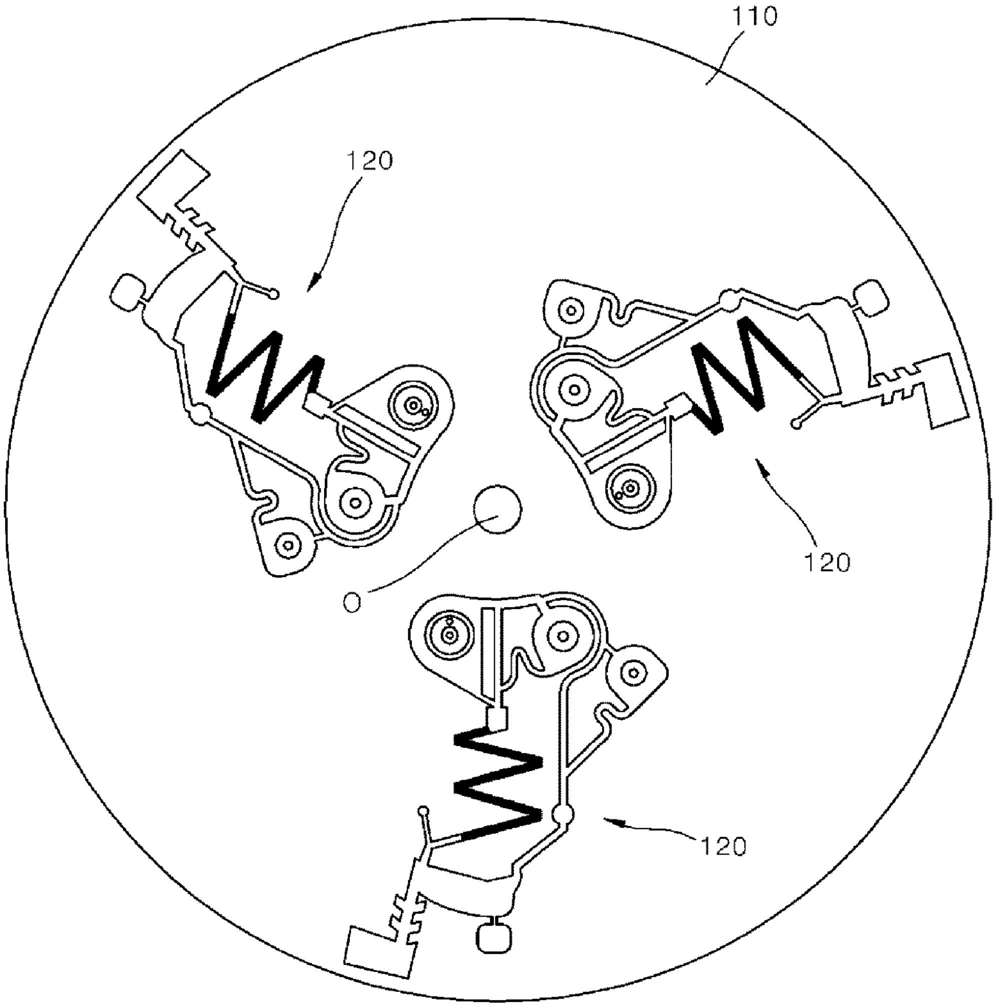
FIG. 2 is a plane view showing the micro-chip for diagnosis (hereinafter, also referred to as a 'diagnosis micro-chip') of FIG. 1.

FIGS. 1 and 2 are a perspective view and a plane view showing a micro-chip for diagnosis (hereinafter, also referred to as a 'diagnosis micro-chip') according to an embodiment of the present disclosure. Referring to FIGS. 1 and 2, the diagnosis micro-chip 110 generally has a disk shape, and a rotation center O is provided at a center of the diagnosis micro-chip 110. The diagnosis micro-chip 110 includes a plurality of unit process parts 120 located apart from the rotation center O in a radial direction and arranged in order in a circumferential direction. In this embodiment, three unit process parts 120 are provided, but in the present disclosure, the number of unit process parts 120 is not limited to three. In the present disclosure, the diagnosis micro-chip 110 may include two or less unit process parts 120 or four or more unit process parts 120. In addition, in this embodiment, the diagnosis micro-chip 110 has a disk shape, but the diagnosis micro-chip 110 of the present disclosure is not limited to the disk shape. The diagnosis micro-chip 110 may be fabricated by, for example, forming a groove pattern in one surface of a polycarbonate (PC) disk with a thickness of about 1 mm by means of a CNC milling machine and then adhering a PC film with a thickness of about 100 μm to the processed surface.

Figure 3:
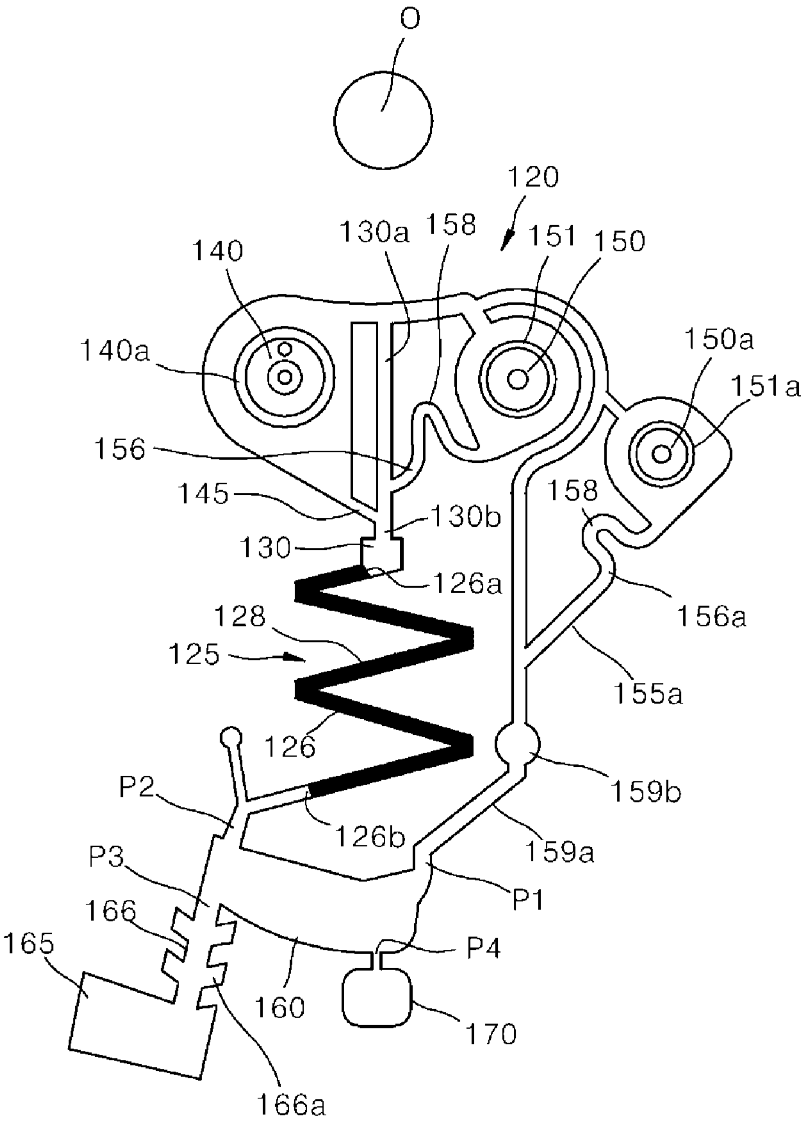
FIG. 3 is a plane view showing a unit process part depicted in FIG. 1.

In FIG. 3, the unit process part 120 depicted in FIGS. 1 and 2 is shown as a plane view together with the rotation center O. Referring to FIG. 3, the unit process part 120 includes a target substance capturing unit 125, a sample storing unit 130, a washing buffer chamber 140, a washing buffer introducing passage 145, an elution buffer chamber 150, an elution buffer flow control passage 156, a reaction solution chamber 150*a*, a reaction solution introducing passage 155*a*, a discharge passage 160, a wasted solution chamber 165, and a target substance chamber 170.

The target substance capturing unit 125 includes a capture passage 126 extending with a zigzag pattern in a radial direction and a capturing means 128 such as silica beads which fills the capture passage 126. In the target substance capturing unit 125, material including a target substance is captured by the capturing means 128 from the sample introduced to the capture passage 126. An inlet 126*a* and an outlet 126*b* are located at both ends of the capture passage 126. The inlet 126*a* is located at an inner side in a radial direction based on the rotation center O, and the outlet 126*b* is located at an outer side in a radial direction. Material including a target substance is absorbed to the capturing means 128 from the sample. In this embodiment, the capturing means 128 is silica beads. Though not shown in detail, a weir structure is formed at a downstream end of the capture passage 126 so that the capturing means 128 may keep received in the capture passage 126.

The sample storing unit 130 has a chamber shape, located inside of the inlet 126*a* of the capture passage 126 in a radial direction and connected to the inlet 126*a* of the capture passage 126. The sample storing unit 130 stores samples. The inner end of the sample storing unit 130 in a radial direction is connected to an extension passage 130*a*. The extension passage 130*a* generally extends along a radial direction, and an outer end thereof in a radial direction is connected to the sample storing unit 130. A valve unit 130*b* configured with a capillary tube valve is provided at a portion of the extension passage 130*a* adjacent to the sample storing unit 130.

The washing buffer chamber 140 has a chamber, located closer to the rotation center O in comparison to the sample storing unit 130. The washing buffer chamber 140 stores a washing buffer. The washing buffer removes components other than the target substance from the material captured by the capturing means 128 by washing the capturing means 128. A washing buffer injection hole is formed in the diagnosis micro-chip 110 to inject a washing buffer into the washing buffer chamber 140. A valve unit 140*a* is prepared around the washing buffer chamber 140 to surround the washing buffer chamber 140. The valve unit 140*a* is a manual valve using a height difference and controls the washing buffer stored in the washing buffer chamber 140 not to easily deviate from the washing buffer chamber 140. Due to a centrifugal force generated when the diagnosis micro-chip 110 rotates based on the rotation center O, the washing buffer stored in the washing buffer chamber 140 deviates from the valve unit 140*a* and is introduced into the washing buffer introducing passage 145.

The washing buffer introducing passage 145 generally extends straightly and connects an outer end of the washing buffer chamber 140 in a radial direction to the extension passage 130*a*. A portion of the washing buffer introducing passage 145 which is connected to the washing buffer chamber 140 is located inside of a portion thereof which is connected to the extension passage 130*a* in a radial direction. In addition, a portion of the washing buffer introducing passage 145 which is connected to the extension passage 130*a* is located inside of the valve unit 130*b* in a radial direction.

The elution buffer chamber 150 has a chamber shape and is located closer to the rotation center O in comparison to the sample storing unit 130. In addition, the elution buffer chamber 150 is located at an opposite side of the washing buffer chamber 140 over the extension passage 130*a*. The elution buffer chamber 150 stores an elution buffer. The elution buffer separates the target substance absorbed to the capturing means 128 from the capturing means 128. An elution buffer injection hole is formed in the diagnosis micro-chip 110 to inject an elution buffer into the elution buffer chamber 150. A valve unit 151 is prepared around the elution buffer chamber 150 to surround the elution buffer chamber 150. The valve unit 151 is a manual valve using a height difference and controls the elution buffer stored in the elution buffer chamber 150 not to easily deviate from the elution buffer chamber 150. Due to a centrifugal force generated when the diagnosis micro-chip 110 rotates based on the rotation center O, the elution buffer stored in the elution buffer chamber 150 deviates from the valve unit 151 and is introduced into the elution buffer flow control passage 156.

The elution buffer flow control passage 156 introduces the elution buffer stored in the elution buffer chamber 150 into the capture passage 126 at an appropriate time. The elution buffer flow control passage 156 extends from the elution buffer chamber 150 and is connected to the extension passage 130*b*. The elution buffer flow control passage 156 generally extends inwards in a radial direction from the elution buffer chamber 150, and then changes its direction with a smooth curve and extends outwards in a radial direction. Accordingly, the elution buffer flow control passage 156 has a flow changing curved portion 158 for changing a flow of the elution buffer from an inside to an outside in a radial direction. A portion of the elution buffer flow control passage 156 which is connected to the extension passage 130*b* is located inside of a portion of the washing buffer introducing passage 145 which is connected to the extension passage 130*a* in a radial direction.

The reaction solution chamber 150*a* is located at an opposite side of the washing buffer chamber 140 together with the elution buffer chamber 150 in a circumferential direction over the extension passage 130*a*. The reaction solution chamber 150*a* stores a reaction solution such as enzyme, primer or other buffers required for a polymerase chain reaction (PCR) process or an isothermal amplification process. The reaction solution enhances gene amplification efficiency. A reaction solution injection hole is formed in the diagnosis micro-chip 110 to inject a reaction solution into the reaction solution chamber 150*a*. A valve unit 151*a* is prepared around the reaction solution chamber 150*a* to surround the reaction solution chamber 150*a*. The valve unit 151*a* is a manual valve using a height difference and controls the reaction solution stored in the reaction solution chamber 150*a* not to easily deviate from the reaction solution chamber 150*a*. Due to a centrifugal force generated when the diagnosis micro-chip 110 rotates based on the rotation center O, the reaction solution stored in the reaction solution chamber 150*a* deviates from the valve unit 151*a* and is then introduced into the reaction solution introducing passage 155*a*.

The reaction solution introducing passage 155*a* includes a reaction solution flow control passage 156*a* and a connection passage 159*a*, which are connected to each other. Through the reaction solution introducing passage 155*a*, the reaction solution stored in the reaction solution chamber 150*a* is introduced into the discharge passage 160 extending from the outlet 126*b* of the capture passage 126.

The reaction solution flow control passage 156*a* extends from the reaction solution chamber 150*a* and is connected to the connection passage 159*a*. The reaction solution flow control passage 156*a* generally extends inwards in a radial direction from the reaction solution chamber 150*a*, and then changes its direction with a smooth curve and extends outwards in a radial direction. Accordingly, the reaction solution flow control passage 156*a* includes a flow changing curved portion 158*a* for changing a flow of the reaction solution from an inside to an outside in a radial direction.

The connection passage 159*a* extends outwards in a radial direction from a downstream end of the reaction solution flow control passage 156*a* and is connected to the discharge passage 160. A valve unit 159*b* is formed on the connection passage 159*a* due to a height difference. The reaction solution flowing in the connection passage 159*a* passes through the valve unit 159*b* if a rotation speed of the diagnosis micro-chip 110 increases.

The discharge passage 160 is located outside of the target substance capturing unit 125 and the connection passage 159*a* in a radial direction, and generally extends along a circumferential direction with respect to the rotation center O. A portion P1 connected to the connection passage 159*a* and a portion P2 connected to the capture passage 126 are respectively formed at inner sides of both circumferential ends of the discharge passage 160 in a radial direction.

The wasted solution chamber 165 is located outside of the discharge passage 160 in a radial direction. The wasted solution chamber 165 is connected to an end of the wasted solution passage 166 extending outwards in a radial direction from the discharge passage 160. A portion P3 where the wasted solution passage 166 and the discharge passage 160 are connected is located to face a portion P2 of the discharge passage 160 which is connected to the capture passage 126. A plurality of capillary tube valves 166*a* formed by height differences are prepared on the wasted solution passage 166. The capillary tube valve 166*a* prevents a solution stored in the wasted solution chamber 165 from flowing out. The wasted solution chamber 165 stores unnecessary components other than the target substance.

The target substance chamber 170 is located out of the discharge passage 160 in a radial direction. A portion P4 where the target substance chamber 170 and the discharge passage 160 are connected is located to face a portion P1 of the discharge passage 160 which is connected to the connection passage 159*a*. The target substance chamber 170 stores the target substance. The target substance stored in the target substance chamber 170 is amplified by a PCR process or an isothermal amplification process. Hereinafter, the target substance amplified by an amplification process such as a PCR process or an isothermal amplification process in the target substance chamber 170 will be called 'genetic material subject to diagnosis'.

Figure 4:
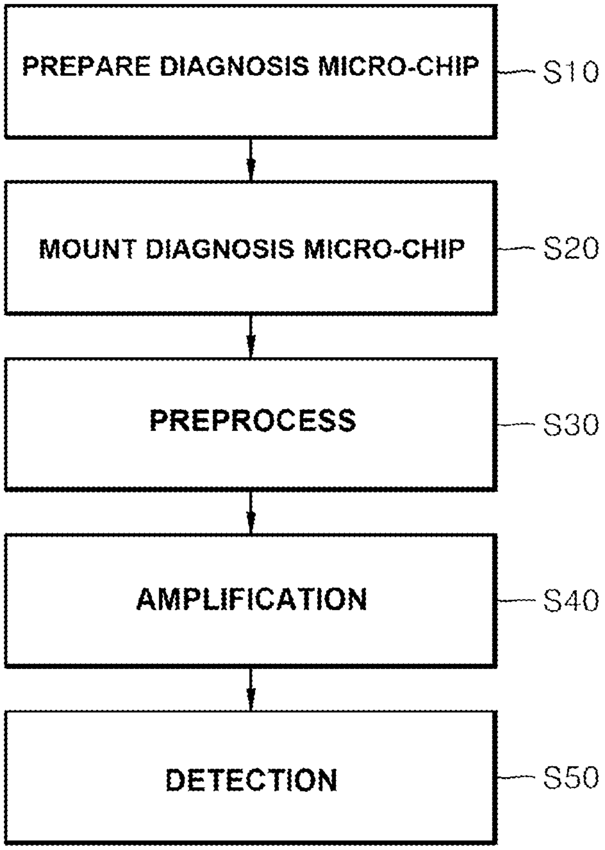
FIG. 4 is a flowchart for illustrating an integrated rotary diagnosis method using the micro-chip for diagnosis of FIG. 1, according to an embodiment of the present disclosure.
Figure 5:
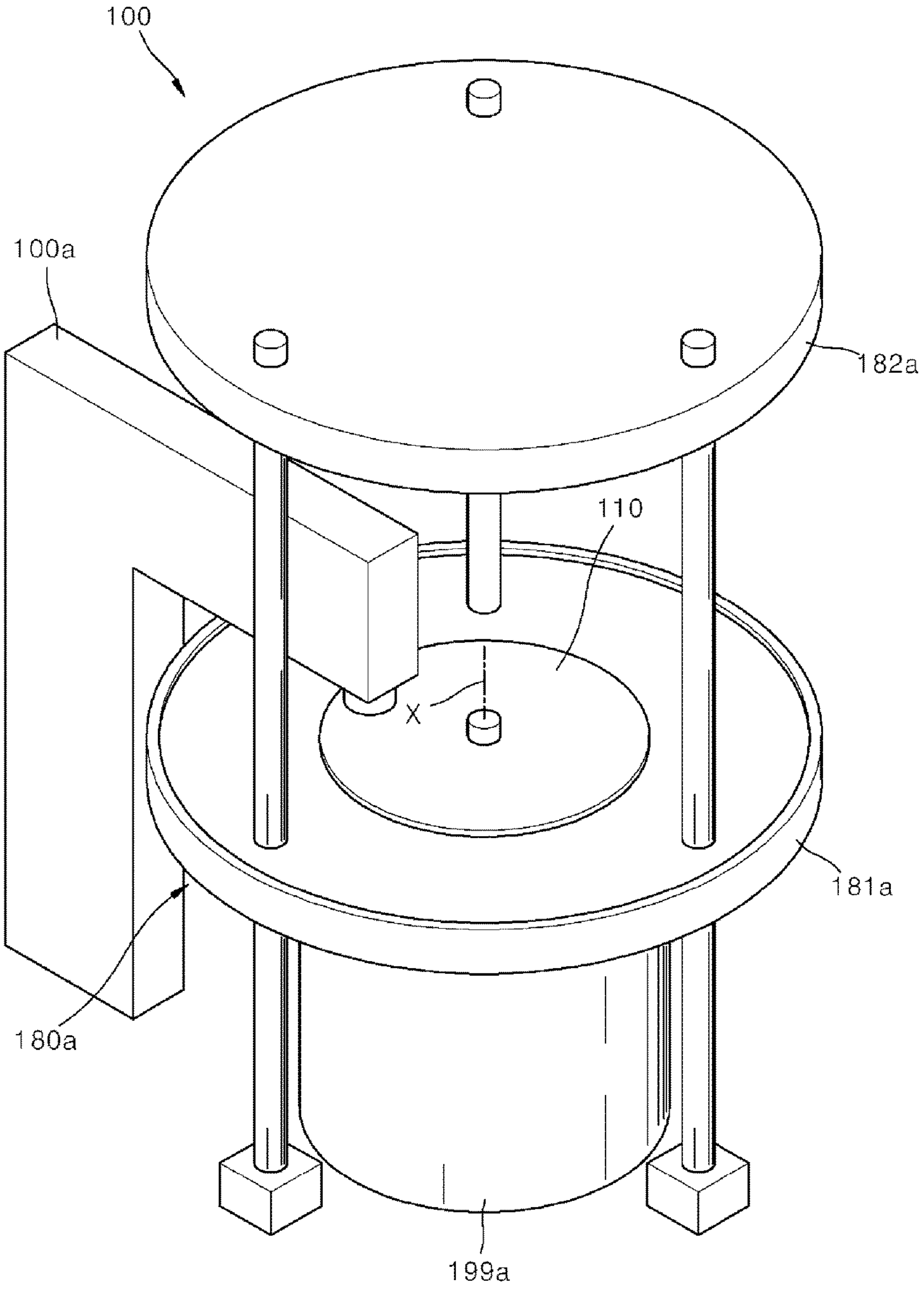
FIG. 5 is a perspective view showing a diagnosis apparatus which performs the diagnosis method depicted in FIG. 4.

Now, an integrated rotary diagnosis method according to an embodiment of the present disclosure by using the diagnosis micro-chip 110 illustrated in FIGS. 1 to 3 will be described with reference to FIG. 4. Prior to explaining the diagnosis method depicted in FIG. 4 in detail, the configuration of a diagnosis apparatus used for the method will be described. FIG. 5 depicts a diagnosis apparatus for performing the diagnosis method of FIG. 4. Referring to FIG. 5, the diagnosis apparatus 100 includes a temperature control unit 180*a* on which the diagnosis micro-chip 110 is placed, a rotation driving unit 199*a* for rotating the diagnosis micro-chip 110 based on a rotary axis X, and a detector 100*a*. The diagnosis apparatus 100 performs an isothermal amplification process, and in this embodiment, reverse transcription loop-mediated isothermal amplification (RT-LAMP) is used as the isothermal amplification process.

Figure 6:
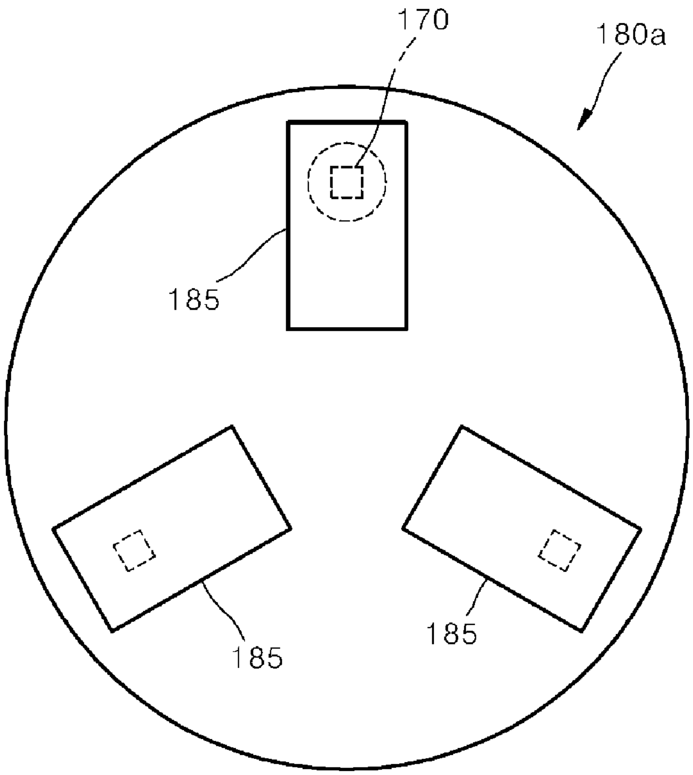
FIG. 6 is a plane view schematically showing a temperature control unit depicted in FIG. 5.

The temperature control unit 180*a* includes a lower member 181*a* and an upper member 182*a*. The temperature control unit 180*a* controls a temperature demanded for the isothermal amplification process. The diagnosis micro-chip 110 is mounted to a top surface of the lower member 181*a* to be rotatable with respect to the temperature control unit 180*a*. The upper member 182*a* moves vertically with respect to the lower member 181*a* and receives the diagnosis micro-chip 110 therein. Referring to FIG. 6, a plurality of heated regions 185 are formed in the temperature control unit 180*a* along a circumferential direction. The heated regions 185 may be formed by an appropriate heating means such as a heating block. In this embodiment, the plurality of heated regions 185 are composed of three heated regions, and these heated regions 185 correspond to three unit process parts 120.

Figure 7:
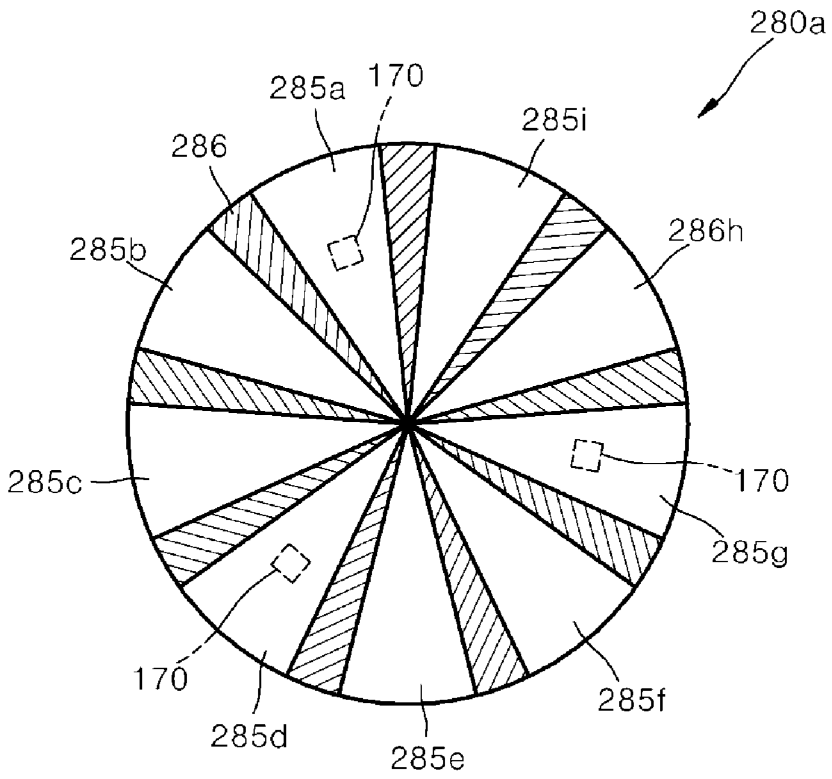
FIG. 7 is a plane view schematically showing another example of the temperature control unit depicted in FIG. 5.

In this embodiment, the diagnosis apparatus 100 performs an isothermal amplification process. However, different from the above, the diagnosis apparatus 100 may also perform a PCR process instead of the isothermal amplification process. FIG. 7 shows an embodiment of the temperature control unit for performing the PCR process. Referring to FIG. 7, a plurality of heated regions 285*a*, 285*b*, 285*c*, 285*d*, 285*e*, 285*f*, 285*g*, 285*h*, 285*i* are formed in the temperature control unit 280*a* in order along a circumferential direction. Between adjacent two heated regions among the plurality of heated regions 285*a*, 285*b*, 285*c*, 285*d*, 285*e*, 285*f*, 285*g*, 285*h*, 285*i*, an insulator or a cooling unit 286 is provided. Each of the heated regions 285*a*, 285*b*, 285*c*, 285*d*, 285*e*, 285*f*, 285*g*, 285*h*, 285*i* may be formed by an appropriate heating means such as a heating block. The plurality of heated regions 285*a*, 285*b*, 285*c*, 285*d*, 285*e*, 285*f*, 285*g*, 285*h*, 285*i* includes a first heated region 285*a*, a second heated region 285*b*, a third heated region 285*c*, a fourth heated region 285*d*, a fifth heated region 285*e*, a sixth heated region 285*f*, a seventh heated region 285*g*, an eighth heated region 285*h*, and a ninth heated region 285*i* along a circumferential direction. The first, fourth and seventh heated regions 285*a*, 285*d*, 285*g* provide a temperature demanded for a denaturizing step in the PCR process. The second, fifth and eighth heated regions 285*b*, 285*e*, 285*h* give a temperature demanded for a coupling step in the PCR process. The third, sixth and ninth heated regions 285*c*, 285*f*, 285*i* provide a temperature demanded for a stretching step in the PCR process. The first, second and third heated regions 285*a*, 285*b*, 285*c* form a single unit temperature control region, the fourth, fifth and sixth heated regions 285*d*, 285*e*, 285*f* form another unit temperature control region, and the seventh, eighth and ninth heated regions 285*g*, 285*h*, 285*i* form still another unit temperature control region. In other words, the temperature control unit 280 has three unit temperature control regions, which respectively provide a temperature required for the PCR process corresponding to three unit process parts 120 located at the diagnosis micro-chip 110 along a circumferential direction.

The rotation driving unit 199*a* includes a rotation-driving motor which rotates the rotation center O of the diagnosis micro-chip 110 based on the rotary axis X. The rotation driving unit 199*a* rotates the diagnosis micro-chip 110 to generate a centrifugal force required for the movement of liquid, and when the isothermal amplification process or the PCR process is performed, the rotation driving unit 199*a* rotates the diagnosis micro-chip 110 so that each target substance chamber 170 of the diagnosis micro-chip 110 is located at a heated region required for the temperature control units 180*a*, 280*a*.

Referring to FIG. 4 again, the diagnosis method includes a diagnosis micro-chip preparing step (S10), a diagnosis micro-chip mounting step (S20), a preprocess step (S30), an amplifying step (S40), and a detecting step (S50).

Figure 8:
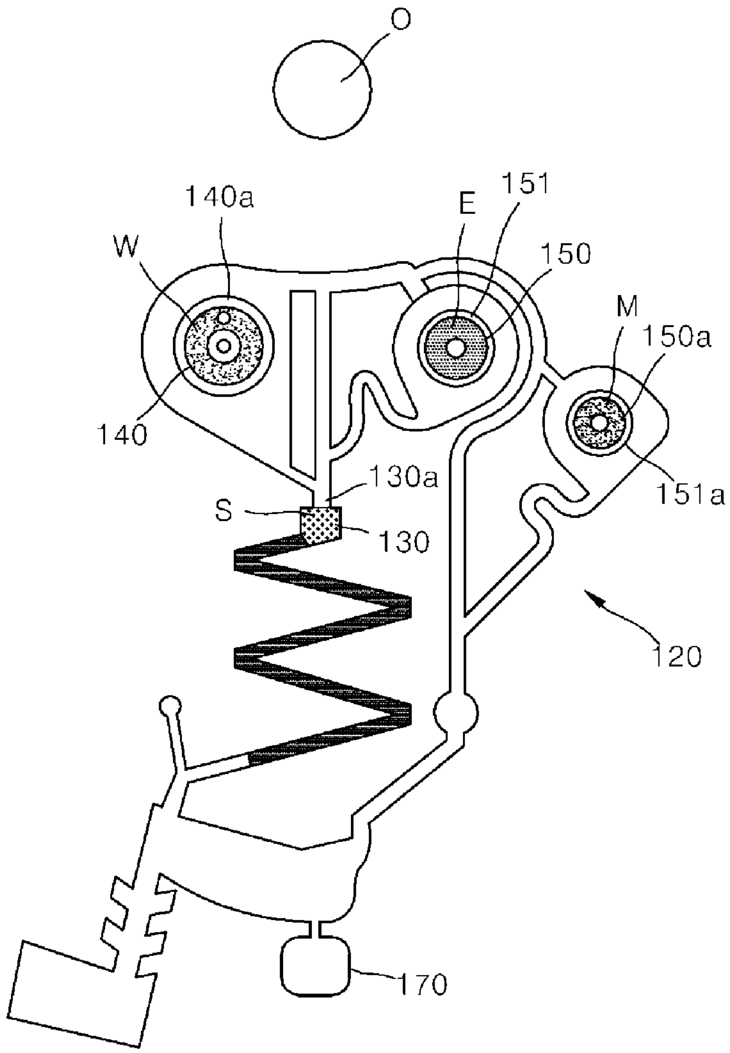
FIG. 8 is a diagram showing a state where a sample, a washing buffer, an elution buffer and a reaction solution are injected into the unit process part through a diagnosis micro-chip preparing process.

In the diagnosis micro-chip preparing step (S10), a sample, a washing buffer, an elution buffer and a reaction solution are injected into the diagnosis micro-chip 110 as shown in FIG. 1. FIG. 8 shows a state in which a sample, a washing buffer, an elution buffer and a reaction solution are injected in the unit process part 120. Referring to FIG. 8, the sample S is stored in the sample storing unit 130, the washing buffer W is stored in the washing buffer chamber 140, the elution buffer E is stored in the elution buffer chamber 150, and the reaction solution M is stored in the reaction solution chamber 150*a*.

In the diagnosis micro-chip mounting step (S20), the diagnosis micro-chip 110 into which the sample, the washing buffer, the elution buffer and the reaction solution are injected through the diagnosis micro-chip preparing step (S10) is mounted to be received in the temperature control unit 180*a* of the diagnosis apparatus 100. At this time, the rotation center O of the diagnosis micro-chip 110 is located on the rotary axis X. The diagnosis micro-chip 110 received in the temperature control unit 180*a* is connected to the rotation driving unit 199*a* to be rotatable with respect to the rotary axis X.

Figure 9:
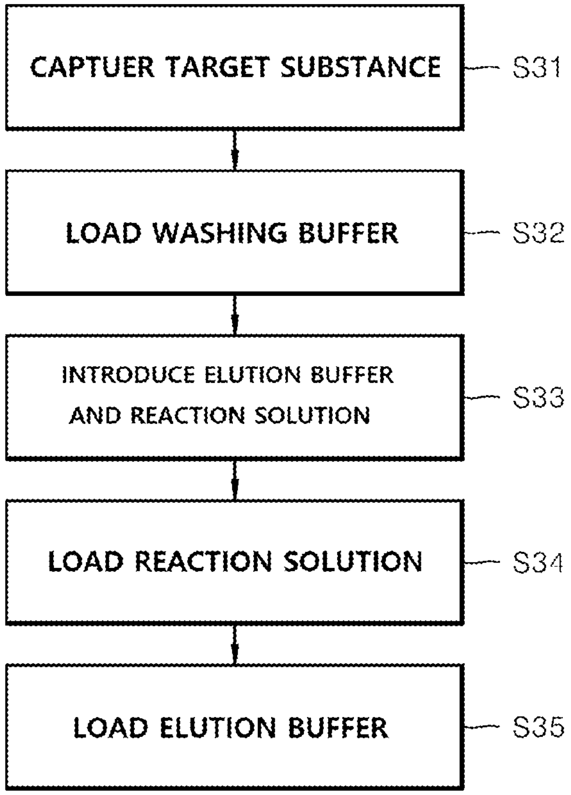
FIG. 9 is a flowchart for illustrating a detailed procedure of the preprocess step depicted in FIG. 4.

In the preprocess step (S30), a target substance included in the sample S stored in the sample storing unit 130 of the diagnosis micro-chip 110 is separated from other components and stored in the target substance chamber 170 together with the reaction solution. Detailed processes of the preprocess step (S30) are depicted as a flowchart in FIG. 9. Referring to FIG. 9, the preprocess step (S30) includes a target substance capturing step (S31), a washing buffer loading step (S32), an elution buffer and reaction solution introducing step (S33), a reaction solution loading step (S34), and an elution buffer loading step (S35). FIGS. 10 to 14 depict a state of the unit process part 120 at each step (S31, S32, S33, S34, S35).

Figure 10:
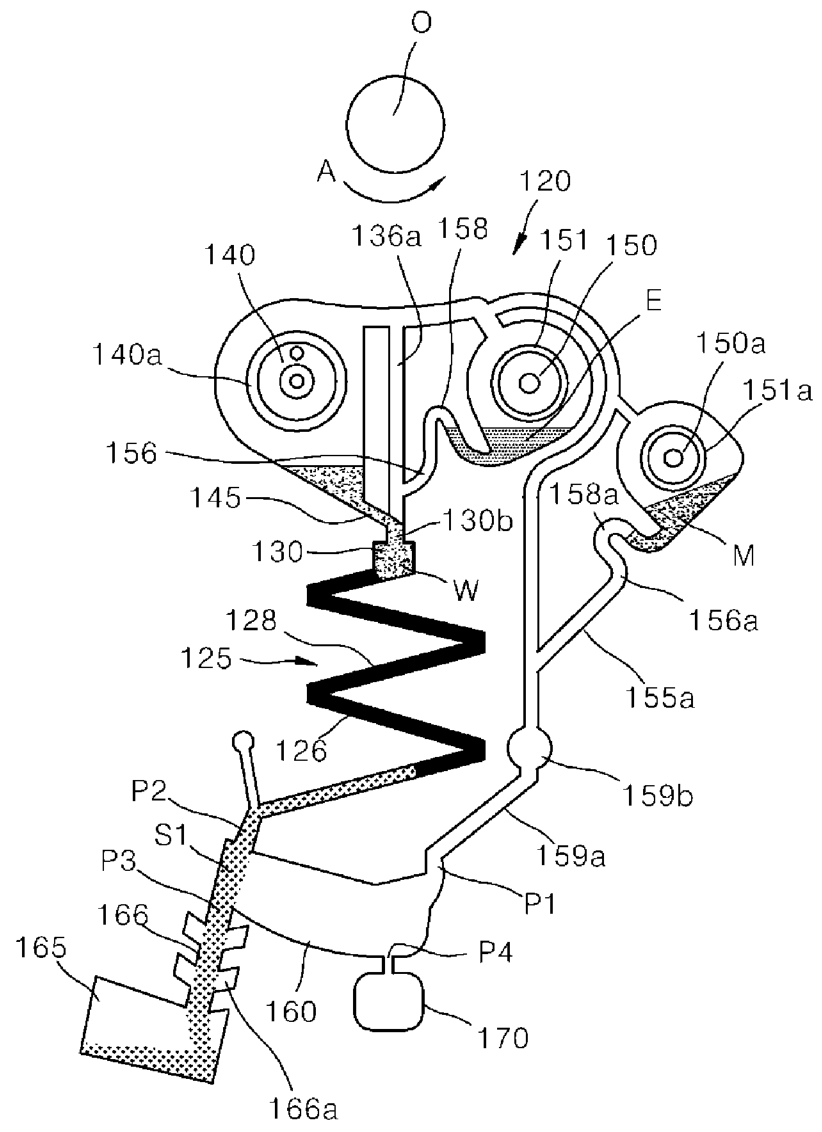
FIGS. 10 to 14 are diagrams respectively showing a state of the unit process part corresponding to each step depicted in FIG. 9.

The target substance capturing step (S31) is performed by rotating the diagnosis micro-chip 110 based on the rotation center O at a first rotation speed (for example, 5000 RPM) for a predetermined time (for example, 10 seconds) in a first rotation direction A. Here, the first rotation direction A represents a rotation direction in which the wasted solution chamber 165 moves toward the target substance chamber 170. In an initial state of the target substance capturing step (S31) where the rotation speed increases, the sample S stored in the sample storing unit 130, the washing buffer W stored in the washing buffer chamber 140, the elution buffer E stored in the elution buffer chamber 150 and the reaction solution M stored in the reaction solution chamber 150*a* respectively move over the valve units 130*a*, 140*a*, 151, 151*a*. FIG. 10 shows a state of the unit process part 120 at the target substance capturing step (S31). Referring to FIG. 10, while the sample S passes by the target substance capturing unit 125, material including a target substance is absorbed to the capturing means 128 due to a centrifugal force, and other unnecessary unabsorbed substances S1 are introduced through the discharge passage 160 into the wasted solution chamber 165. While passing along the discharge passage 160, the unnecessary unabsorbed substances S1 do not flow toward the target substance chamber 170 but are entirely introduced into the wasted solution chamber 165 due to the rotation direction A. In the target substance capturing step (S31), the washing buffer W passes through the cleaning solution introducing passage 145 and is introduced into the target substance capturing unit 125 in succession to the sample S. In the target substance capturing step (S31), the elution buffer E keeps its state of being moved to a location before the flow changing curved portion 158 on the elution buffer flow control passage 156. In the target substance capturing step (S31), the reaction solution M keeps a state of being moved to a location before the flow changing curved portion 158*a* on the reaction solution flow control passage 156*a*. After the target substance capturing step (S31), the washing buffer loading step (S32) is performed.

Figure 11:
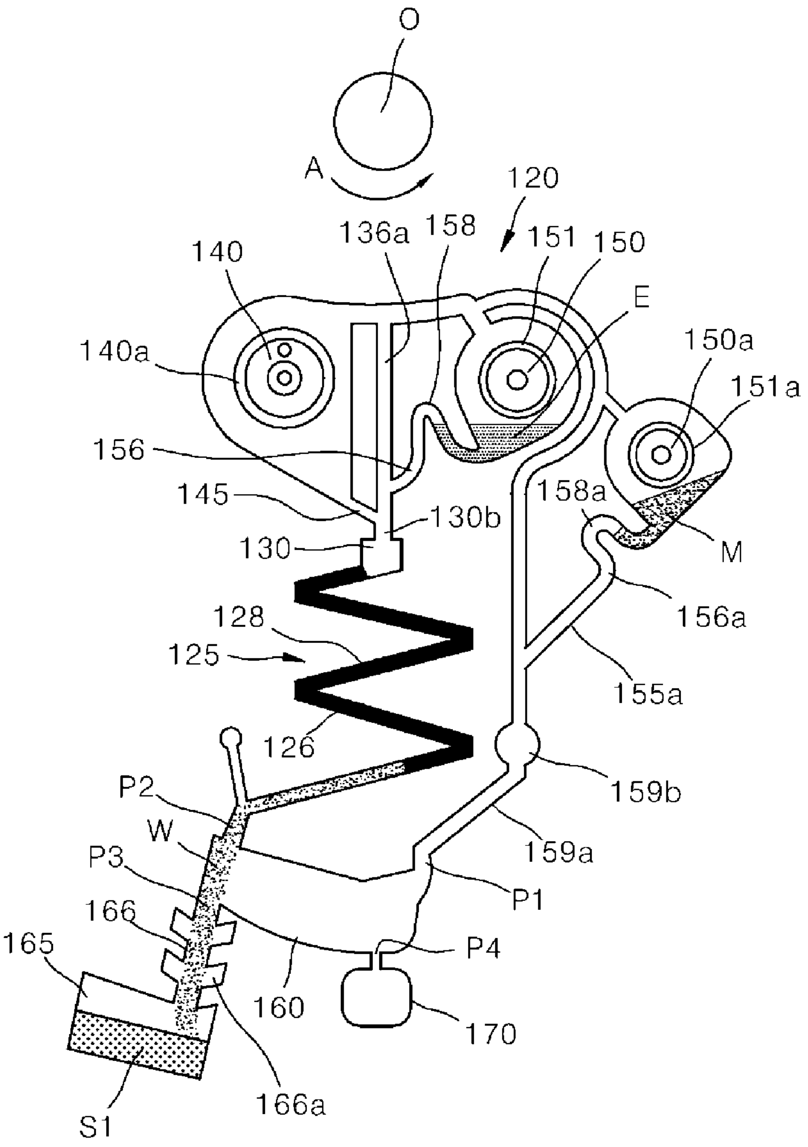

The washing buffer loading step (S32) is performed by rotating the diagnosis micro-chip 110 based on the rotation center O at a second rotation speed (for example, 5000 RPM identical to the first rotation speed) for a predetermined time (for example, 4 minutes) in the first rotation direction A. In the washing buffer loading step (S32), the washing buffer W passes through the target substance capturing unit 125 and then is introduced into the wasted solution chamber 165 across the discharge passage 160 due to a centrifugal force as shown in FIG. 11. While the washing buffer W passes through the discharge passage 160, due to its rotation direction A, the washing buffer W does not flow toward the target substance chamber 170 but is entirely introduced into the wasted solution chamber 165. While passing through the target substance capturing unit 125, the washing buffer W removes components other than the target substance from the material captured by the target substance capturing unit 125 by washing. After the washing buffer loading step (S32), the elution buffer and reaction solution introducing step (S33) is performed.

Figure 12:
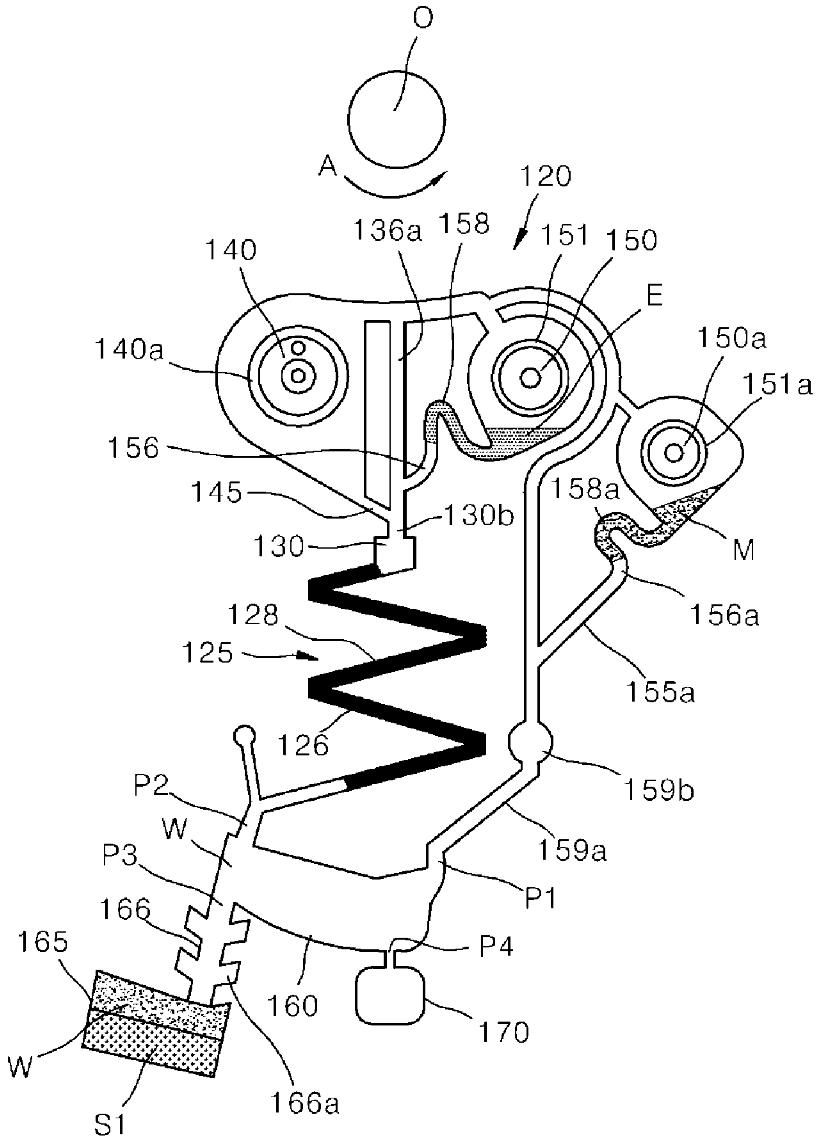

The elution buffer and reaction solution introducing step (S33) is performed by rapidly decreasing the rotation speed of the diagnosis micro-chip 110 to zero (0). FIG. 12 shows a state of the unit process part 120 at the elution buffer and reaction solution introducing step (S33). Referring to FIG. 12, in the elution buffer and reaction solution introducing step (S33), the elution buffer E has already passed through the flow changing curved portion 158 of the elution buffer flow control passage 156, and the reaction solution M has already passed through the flow changing curved portion 158*a* of the reaction solution flow control passage 156*a*. The passage of the elution buffer E through the flow changing curved portion 158 and the passage of the reaction solution M through the flow changing curved portion 158*a* are caused by the decrease of a centrifugal force due to rapid deceleration. After the elution buffer and reaction solution introducing step (S33), the reaction solution loading step (S34) is performed.

Figure 13:
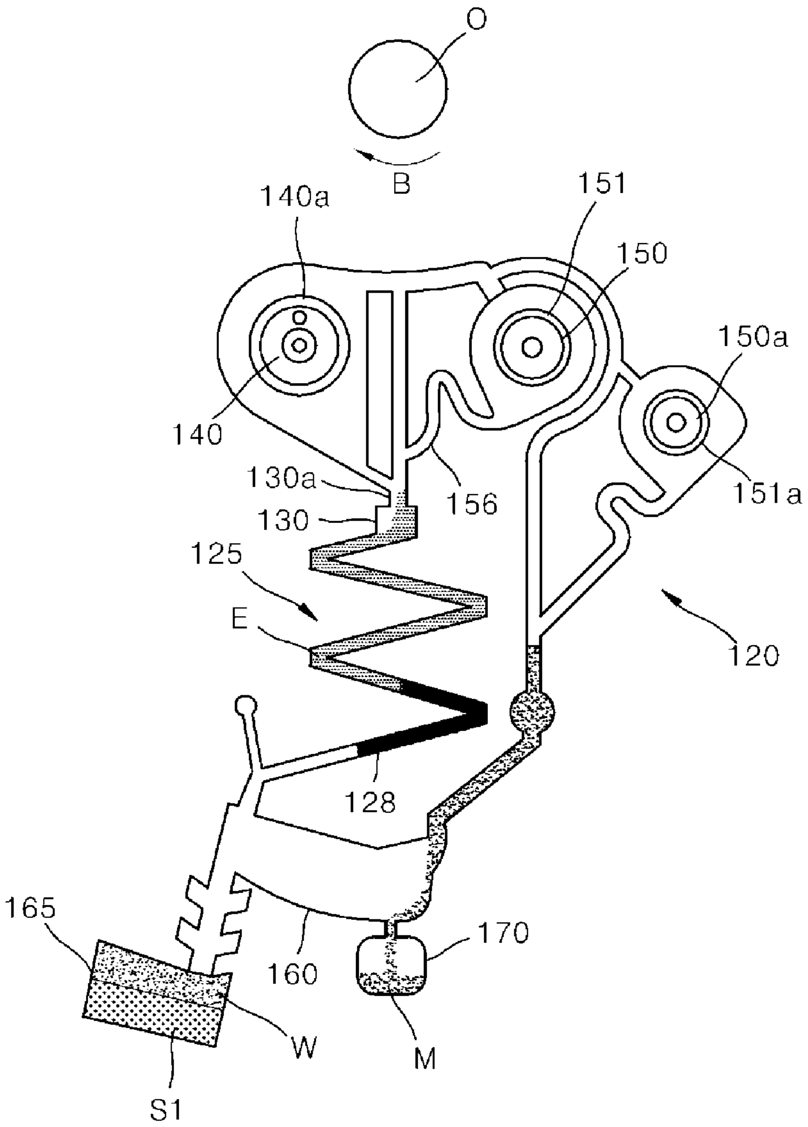

The reaction solution loading step (S34) is performed by rotating the diagnosis micro-chip 110 based on the rotation center O at a third rotation speed (for example, 5000 RPM) for a predetermined time (for example, 30 seconds) in a second rotation direction B opposite to the first rotation direction A. FIG. 13 shows a state of the unit process part 120 at the reaction solution loading step (S34). Referring to FIG. 13, the reaction solution M is introduced into the target substance chamber 170 after passing through the connection passage 159*a* and the discharge passage 160. While the reaction solution M is passing through the discharge passage 160, due to its rotation direction B, the reaction solution M does not flow toward the wasted solution chamber 165 but is entirely introduced into the target substance chamber 170. In addition, while passing through the target substance capturing unit 125, the elution buffer E separates the target substance captured by the target substance capturing unit 125 from the capturing means 128. After the reaction solution loading step (S34), the elution buffer loading step (S35) is performed.

Figure 14:
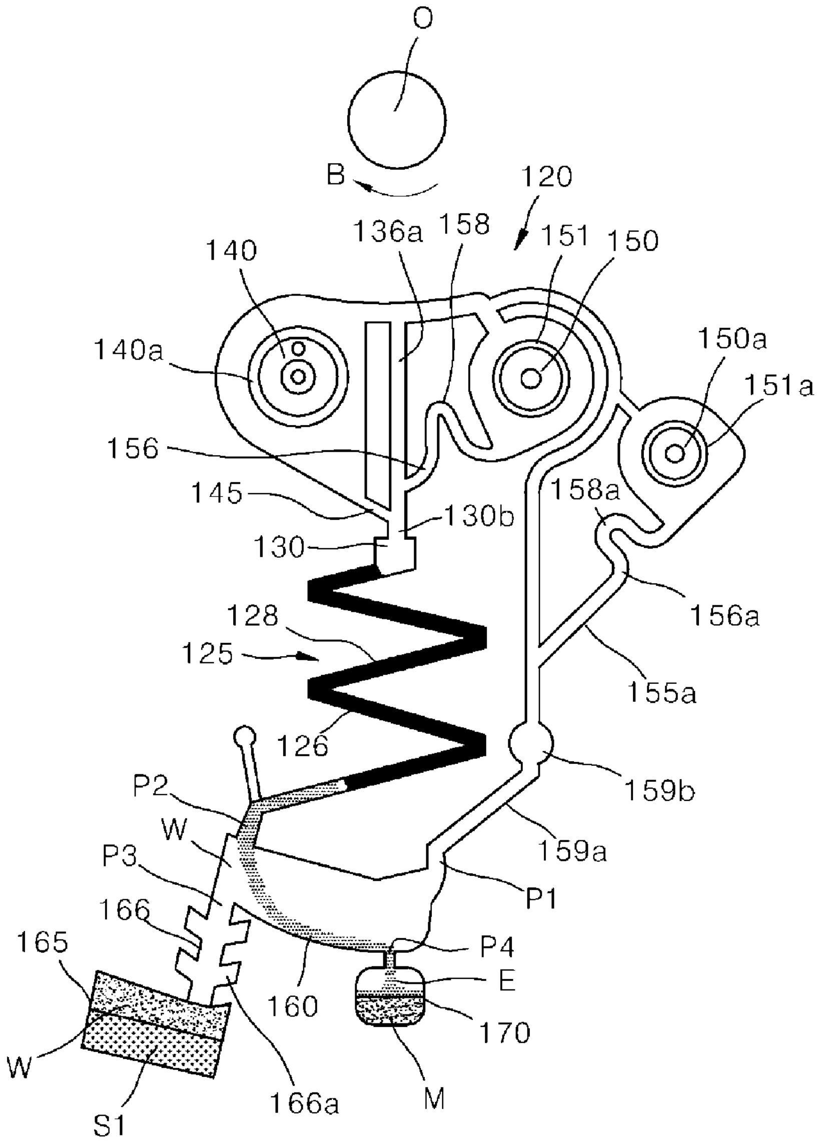

The elution buffer loading step (S35) is performed by rotating the diagnosis micro-chip 110 based on the rotation center O at a fourth rotation speed (for example, 5000 RPM identical to the third rotation speed) for a predetermined time (for example, 4 minutes) in the second rotation direction B. FIG. 14 shows a state of the unit process part 120 at the elution buffer loading step (S35). Referring to FIG. 14, after passing through the target substance capturing unit 125 due to the centrifugal force, the elution buffer E passes through the discharge passage 160 together with the target substance and is introduced into the target substance chamber 170, so as to be mixed with the reaction solution M introduced before. While the elution buffer E is passing through the discharge passage 160, due to its rotation direction B, the elution buffer E is not introduced into the wasted solution chamber 165 but is entirely guided to the target substance chamber 170 as shown in the figures. Through the elution buffer loading step (S35), the elution buffer E is entirely introduced into the target substance chamber 170.

Referring to FIG. 4 again, after the preprocess step (S30) is completed, the amplifying step (S40) is performed. In the amplifying step (S40), an isothermal amplification process such as real-time RT-LAMP is used or a PCR process is used. In case of the isothermal amplification process, the temperature control unit 180*a* as shown in FIG. 6 may be used. Referring to FIG. 6, the isothermal amplification process is performed by suitably controlling the temperature of the target substance received in each target substance chamber 170 of the diagnosis micro-chip 110 by means of the corresponding heated region 185. In case of the PCR process, the temperature control unit 280*a* as shown in FIG. 7 may be used. Referring to FIG. 7, the PCR process includes a denaturizing step, a coupling step and a stretching step. The denaturizing step is performed by locating each target substance chamber 170 of the diagnosis micro-chip 110 respectively at the first, fourth and seventh heated regions 285*a*, 285*d*, 285*g* which give the temperature of the denaturizing step. The coupling step is performed by rotating the diagnosis micro-chip 110 by a predetermined angle so that each target substance chamber 170 is located at the second, fifth and eighth heated regions 285*b*, 285*e*, 285*h* which give the temperature of the coupling step. After the coupling step is completed, the stretching step is performed by rotating the diagnosis micro-chip 110 by a predetermined angle so that each target substance chamber 170 is located at the third, sixth and ninth heated regions 285*c*, 285*f*, 285*i* which give the temperature of the stretching step. After the amplifying step (S40), the detecting step (S50) is performed.

The detecting step (S60) is performed by means of fluorescence detection with respect to a material subject to diagnosis, which is received in the target substance chamber 170, by using the detector 100*a*.

Figure 15:
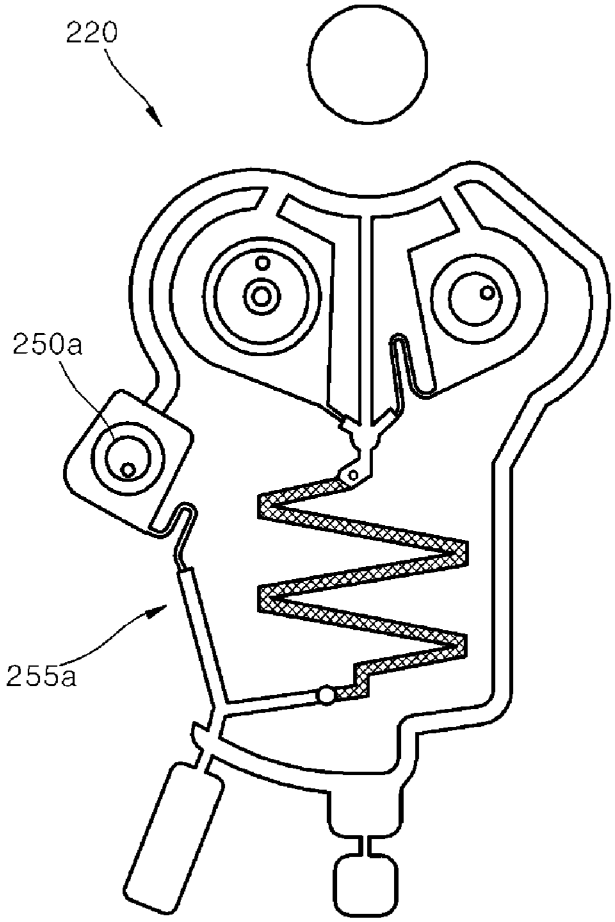
FIG. 15 is a plane view showing a unit process part according to another embodiment of the present disclosure.

FIG. 15 depicts a unit process part according to another embodiment of the present disclosure. Referring to FIG. 15, the unit process part 220 is substantially identical to the unit process part 120 depicted in FIG. 3, except that the reaction solution introducing passage 255*a* extending from the reaction solution chamber 250*a* is located to be connected together with the capture passage 126. The diagnosis method illustrated in FIG. 4 may also be applied to the diagnosis micro-chip having the unit process part 220 depicted in FIG. 15.

While the present disclosure has been described with respect to the specific embodiments, the present disclosure is not limited thereto. It will be apparent to those skilled in the art that various changes and modifications may be made without departing from the spirit and scope of the invention as defined in the following claims.

What is claimed is:

1. A micro-chip for diagnosis, comprising:

a unit process part located apart from a rotation center, wherein the unit process part includes:

a target substance capturing unit having a capture passage with an inlet and an outlet located outside of the inlet in a radial direction, and a capturing means filling the capture passage;

a sample storing unit located farther inside relative to the target substance capturing unit in a radial direction, connected to the inlet of the capture passage and having an inner space in which a sample is stored;

a washing buffer chamber located farther inside relative to the target substance capturing unit in a radial direction, connected to the inlet of the capture passage and having an inner space in which a washing buffer is stored;

an elution buffer chamber located farther inside relative to the target substance capturing unit in a radial direction, connected to the inlet of the capture passage and having an inner space in which an elution buffer is stored;

a reaction solution chamber having a space in which a reaction solution, required for a polymerase chain reaction (PCR) process or an isothermal amplification process, is stored;

a discharge passage located farther outside relative to the target substance capturing unit and the reaction solution chamber in a radial direction, extending along a circumferential direction and connected to the target substance capturing unit and the reaction solution chamber, the discharge passage having first and second sides opposite each other in the circumferential direction;

a wasted solution chamber located farther outside relative to the discharge passage in a radial direction and connected to the discharge passage; and a target substance chamber located farther outside relative to the discharge passage in a radial direction and connected to the discharge passage, wherein a portion of the discharge passage to which the wasted solution chamber is connected and a portion of the discharge passage to which the target substance chamber is connected are separated from each other along the circumferential direction, wherein a portion of the discharge passage, which is connected to the capture passage, and the portion of the discharge passage, which is connected to the wasted solution chamber, are located on the first side and across from each other in a radial direction, and further wherein a portion of the discharge passage, which is connected to the reaction solution chamber, and the portion of the discharge passage, which is connected to the target substance chamber, are located on the second side and across from each other in a radial direction.

2. The micro-chip for diagnosis according to claim 1, wherein the portion of the discharge passage, which is connected to the target substance chamber, and the portion of the discharge passage, which is connected to the wasted solution chamber, are respectively located at both ends of the discharge passage in the circumferential direction.

3. The micro-chip for diagnosis according to claim 1, wherein the capture passage connects the inlet and the outlet in a zigzag pattern.

4. The micro-chip for diagnosis according to claim 1, wherein the unit process part further includes a valve unit configured to encircle the washing buffer chamber, the elution buffer chamber and the reaction solution chamber, and wherein the valve unit is a manual valve.

5. The micro-chip for diagnosis according to claim 1, wherein the unit process part further includes an elution buffer flow control passage for introducing the elution buffer stored in the elution buffer chamber to the target substance capturing unit, and wherein the elution buffer flow control passage includes a flow changing curved portion for changing a flow of the elution buffer from an inside to an outside in a radial direction.

6. The micro-chip for diagnosis according to claim 1, wherein the unit process part further includes a reaction solution flow control passage extending from the reaction solution chamber, and wherein the reaction solution flow control passage includes a flow changing curved portion for changing a flow of the reaction solution discharging from the reaction solution chamber from an inside to an outside in a radial direction.

7. The micro-chip for diagnosis according to claim 1, wherein the unit process part further includes a capillary tube valve formed at a wasted solution passage which connects the discharge passage and the wasted solution chamber.

* * * * *